（12) United States Patent
Baranton et al.

(10) Patent No.: US 9,289,119 B2
(45) Date of Patent: Mar. 22, 2016

(54) DEVICE FOR DETERMINING AT LEAST ONE SIGHT PARAMETER OF A SUBJECT IN A PLURALITY OF VIEWING DIRECTIONS

(71) Applicants: Konogan Baranton, Charenton le Pont (FR); Guilhem Escalier, Charenton le Pont (FR)

(72) Inventors: Konogan Baranton, Charenton le Pont (FR); Guilhem Escalier, Charenton le Pont (FR)

(73) Assignee: ESSILOR INTERNATIONAL (COMPAGNIE GENERALE D'OPTIQUE), Charenton le Pont (FR)

( * ) Notice: Subject to any disclaimer, the term of this patent is extended or adjusted under 35 U.S.C. 154(b) by 91 days.

(21) Appl. No.: 14/366,192

(22) PCT Filed: Dec. 6, 2012

(86) PCT No.: PCT/FR2012/052821
§ 371 (c)(1),
(2) Date: Jun. 17, 2014

(87) PCT Pub. No.: WO2013/093279
PCT Pub. Date: Jun. 27, 2013

(65) Prior Publication Data
US 2014/0327883 A1    Nov. 6, 2014

(30) Foreign Application Priority Data

Dec. 22, 2011 (FR) .................................. 11 04036

(51) Int. Cl.
| A61B 3/10 | (2006.01) |
| A61B 3/02 | (2006.01) |
| A61B 3/103 | (2006.01) |
| A61B 3/00 | (2006.01) |
| A61B 3/028 | (2006.01) |
| A61B 3/036 | (2006.01) |
| A61B 3/15 | (2006.01) |

(52) U.S. Cl.
CPC ............ *A61B 3/103* (2013.01); *A61B 3/0083* (2013.01); *A61B 3/028* (2013.01); *A61B 3/036* (2013.01); *A61B 3/1035* (2013.01); *A61B 3/152* (2013.01)

(58) Field of Classification Search
USPC .................................. 351/221, 237, 239, 243
See application file for complete search history.

(56) References Cited

U.S. PATENT DOCUMENTS

| 3,982,827 A | 9/1976 | Gambs |
| 5,444,504 A | 8/1995 | Kobayashi et al. |
| 2008/0151185 A1 | 6/2008 | Saito et al. |

FOREIGN PATENT DOCUMENTS

| EP | 0 326 760 A2 | 8/1989 |
| EP | 1 882 444 A1 | 1/2008 |

OTHER PUBLICATIONS

International Search Report, dated Mar. 26, 2013, from corresponding PCT application.

*Primary Examiner* — Jack Dinh
(74) *Attorney, Agent, or Firm* — Young & Thompson (57) ABSTRACT

Device for determining at least one sight parameter of a subject, includes stimulation elements for stimulating the sight of the subject in a predetermined viewing direction, elements for ophthalmological measurement of at least one sight parameter of a subject, the elements for ophthalmological measurement having at most one optical measurement axis for each eye, at least one optical conjugation system, arranged between the ophthalmological measurement apparatus and the right eye and/or left eye of a subject, and a system for aligning the optical conjugation system, so as to optically conjugate a point Y and a point E, the point Y intended to coincide with the optical center of rotation of the eye concerned, the point E being situated on the optical measurement axis, so as to align the image of the optical measurement axis with the ocular axis of the right or left eye in a plurality of viewing directions.

18 Claims, 6 Drawing Sheets

DEVICE FOR DETERMINING AT LEAST ONE SIGHT PARAMETER OF A SUBJECT IN A PLURALITY OF VIEWING DIRECTIONS

TECHNICAL FIELD OF THE INVENTION

Generally, the present invention relates to the field of optometric devices and methods. More particularly, the invention relates to an optometric apparatus for determining the various values of the prescription of a lens for a pair of spectacles for progressive or multifocal visual correction, or for a pair of spectacles intended for near-vision correction (reading glasses), which values are associated with the measurement of differentiated ocular refraction for a plurality of gazes and in particular a far-vision gaze and a near-vision gaze. These measurements are intended to be used for the optical design and the manufacture of the refracting faces of corrective lenses for pairs of progressive or multifocal spectacles, or for pairs of spectacles intended to correct near vision (including non-prescription glasses and reading glasses), whether it is a question of passive lenses or lenses having electronically controlled variable optical powers.

PRIOR ART

Over the last fifty odd years the market for corrective multifocal and progressive spectacle lenses has experienced considerable growth. A corrective multifocal lens has at least two separate corrective powers in two zones of the corrective lens corresponding to two vision distances. A corrective progressive lens has an optical power that varies over the surface of the lens, varying, for example in the case of correction of presbyopia, from a zone in which the spherical correction is small for far vision (FV) to a zone in which the spherical correction is greater for near vision (NV). A corrective progressive lens generally provides an average correction for a vision distance intermediate between the far-vision and the near-vision distances. Corrective multifocal or progressive spectacle lenses make it possible for the subject to benefit from an optical power correction that is adapted to various vision distances without changing spectacles. In order to determine the parameters of corrective multifocal lenses or of corrective progressive lenses, binocular or monocular optometric apparatuses are used to measure the near-vision and far-vision optical correction to apply. Optometric apparatuses employing the measurement of the reflection and/or refraction of a light beam from an eye thus allow FV/NV differentiated power correction (or sphere) to be measured, i.e. the near-vision and far-vision correction to be applied to the measured eye. Corrective progressive or multifocal lenses are not only able to correct an optical power error but also other visual defects, in particular astigmatism. Based on the same ocular reflection and/or refraction measuring principle, certain optometric apparatuses allow astigmatism correcting parameters (cylinder and axis), and/or higher-order correcting parameters, to be measured (see standard ISO 24157: 2008, which specifies standardized methods allowing aberrations in the human eye to be reported).

Currently, FV/NV differentiated ocular reflection and/or refraction measurements are only carried out manually. An optometrist uses a test lens to determine the various values of the prescription of the corrective lenses.

In conventional optometric apparatuses, an optical system inserted on the ocular axis adapts optical power in order to modify the visual accommodation distance of a target, the sight line of the gaze remaining horizontal.

Current studies of differentiated (FV/NV) refraction measurements are confronted with the problem of measuring near-vision refraction while following the physiological lowering of the gaze that accompanies this near vision. The patent document EP 1 882 444 describes a method and a device for measuring the visual properties of an eye along various gaze directions, in which an aberrometer is placed on a rotatably movable holder so as to incline the measuring axis in order to align it along a lowered gaze direction. However, if it is desired to use an apparatus that is currently commercially available in a natural lowered or raised gaze direction, it is technically difficult (or even impossible in certain cases) to align the measuring channel with the natural gaze axis of the subject. Specifically, the head of the subject tends to collide with the measuring apparatus. Furthermore, the mechanical elements of existing systems, in particular the translational stages used for centering, are designed to operate in a horizontal plane.

Currently, there are no autorefractor or aberrometer type optometric apparatuses that allow the differentiated far-vision/near-vision refraction effect to be studied along various ocular-axis directions or along various gaze directions.

SUBJECT OF THE INVENTION

The aim of the invention is to improve the precision of ophthalmological measurements that are differentiated as a function of the vision distance of the subject and of the binocular or monocular sight direction of the subject, in order to improve the differentiated correction provided depending on the vision conditions experienced by a subject wearing corrective progressive or multifocal spectacle lenses. In particular, it is sought to obtain measurements of astigmatism that are FV/NV differentiated. Additionally, it is sought to obtain measurements of higher-order aberrations that are also differentiated depending on whether the gaze of the subject is in the FV or NV position.

One of the aims of the invention is to provide an optometric device and a method for carrying out an (objective or subjective) measurement of at least one FV/NV differentiated vision parameter of a subject, as a function of the binocular or monocular sight direction of the subject.

The invention aims to provide an optometric device for measuring at least one vision parameter along various binocular or monocular sight directions of a subject.

In order to remedy the aforementioned drawback of the prior art, the present invention provides a device for determining at least one vision parameter of a subject along a plurality of monocular or binocular sight directions of the subject, said device comprising a binocular or monocular ophthalmological measuring apparatus comprising ophthalmological means for measuring the vision parameter to be determined, which means are able to emit an illuminating optical beam, and to receive a measuring optical beam along at least one measuring optical axis aligned with a preset sight direction of the eye in question, visual stimulating means able to generate a stimulating optical beam along a stimulating optical axis aligned with said preset sight direction of the eye in question, and head-supporting means able to receive the head of a subject and to keep it in a set posture.

More particularly, there being defined an ellipse having a first focal point on said measuring optical axis and a second focal point, according to the invention a device is provided comprising at least one optical aligning system placed between the ophthalmological measuring means and the eye in question, said optical aligning system being able to reflect said illuminating and measuring optical beams between the focal points of the ellipse. According to the invention, the device furthermore comprises adjusting means able to modify the relative position of said optical aligning system relative to the head-supporting means so as to bring the second focal point into the vicinity of the center of rotation of the eye in question of the subject. According to the invention, said optical aligning system comprises first reflective optical means and second reflective optical means, said first reflective optical means being tangent to said ellipse at a first point in a first sight direction and at least one other point in at least one other sight direction of the eye in question, and said second reflective optical means being mounted so as to be rotatably movable about the first focal point between a first position in which the optical aligning system aligns said first sight direction with the measuring optical axis and at least one other position in which the optical aligning system aligns said at least one other sight direction of the eye in question with the measuring optical axis.

The following are other nonlimiting and advantageous features of the device for determining at least one vision parameter of a subject along a plurality of monocular or binocular sight directions of the subject, according to the invention:

said first reflective optical means comprise a spherical mirror, a planar mirror, a plurality of planar mirrors, a dichroic plate or a plurality of dichroic plates;

said first reflective optical means comprise a first mirror, and said optical aligning system comprises means for moving the first mirror, which means are able to move the first mirror along a preset trajectory as a function of the binocular or monocular sight direction of the subject;

said means for moving said first mirror comprise a hinged system of link connecting rods and/or a cam and/or a mechanical guiding system;

said preset trajectory is an elliptical trajectory and said first mirror is oriented so as to be tangent to said elliptical trajectory;

said first reflective optical means comprise a first mirror having a first preset position tangent to said ellipse at a first point, and a second mirror having a second preset position tangent to said ellipse at another point.

Alternatively, said first reflective optical means comprise an ellipsoidal mirror, or more generally an optical surface such that the optical conjugate of the point Y is the point E, and said second reflective optical means comprise a second mirror having a non-zero optical power, so that the optical aligning system formed by the first and second mirrors is approximately a focal, i.e. a focal to the first order in the sense of average sphere in the Gauss approximation.

According to certain particular aspects:

said second reflective optical means comprise a planar mirror;

said optical aligning system comprises a means for orienting the second reflective optical means, able to make the second reflective optical means pivot about the first focal point of the ellipse as a function of the binocular or monocular sight direction;

said aligning system comprises means for inclining said optical aligning system, said inclining means being able to orient the plane of the ellipse about an axis passing through its focal points;

said aligning system comprises at least one first preset position associated with a first sight direction, and at least one other preset position associated with said at least one other sight direction;

said first sight direction is a horizontal direction straight in front of the subject, and said at least one other sight direction corresponds to a near-vision sight direction that is inclined relative to the horizontal;

the device comprises a first preset position for said at least one first gaze declination angle and a second preset position for said at least one other gaze declination angle;

the ophthalmological measuring means are able to measure and record at least one vision parameter such as sphere, cylinder, axis, higher-order aberrations, a keratometry and/or corneal topography type parameter, and/or pupil diameter in a first sight direction and in at least one other sight direction, and/or a difference between a vision parameter measured in said first sight direction and measured in said at least one other sight direction.

According to one particular embodiment, said ophthalmological measuring apparatus is a binocular apparatus having a first measuring axis associated with the right eye of the subject and a second measuring axis associated with the left eye of the subject, and said device comprises:

a first optical aligning system according to one of the embodiments of the invention, placed between said binocular ophthalmological measuring apparatus and the right eye of the subject; and a second optical aligning system according to one of the embodiments of the invention, placed between said binocular ophthalmological measuring apparatus and the left eye of said subject.

DETAILED DESCRIPTION OF AN EXAMPLE EMBODIMENT

The following description, given with regard to the appended drawings, by way of nonlimiting example, will allow what the invention consists of and how it can be carried out to be understood.

In the following description, the subject is considered to be sat or stood such that his/her head is straight, i.e. such that the Frankfurt plane of the head of the subject is substantially horizontal. In anatomy, the Frankfurt plane is the reference plane that allows the skull to be studied. Also called the Virchow plane, it passes anteriorly through the orbital floor and posteriorly above the external auditory meatus. The subject is also said to be in an orthostatic position, in which position they make a minimum of effort.

The median or sagittal plane PSAG of the head 30 of the subject is defined as being a vertical plane parallel to an anterior-posterior axis of the head and passing through a point located halfway between the two eyes. The sagittal plane is parallel to the plane of FIG. 1. The gaze axis or sight line DV of the subject is defined as being located in a plane parallel to the sagittal plane of the subject. In the case where the subject looks at the horizon straight in front of him/her at infinity, the sight line is a horizontal line DVI corresponding to the primary gaze axis. The gaze axis of the subject is horizontal in the far-vision position. During the measurement described below, the subject is asked to lower or raise their gaze and/or direct their gaze rightward or leftward (in this case the gaze axis is no longer parallel to the plane PSAG) while keeping their head 30 in the initial orthostatic position. In the case where the subject simply lowers their gaze without any convergence, the sight line DV is a straight line located in a plane parallel to the sagittal plane and inclined relative to a horizontal line. The right ocular axis is defined as being the axis passing through the object focused on by the subject and the center of the exit pupil (i.e. the image of the real pupil produced by the cornea) of the right eye. Other definitions are possible, for example, the right ocular axis may be taken to be a straight line passing through the center of rotation of the right eye and through the center of the pupil of the right eye or even to be the axis connecting the object focused on to its corresponding image on the retina. All these definitions give approximately the same axis. Likewise, the left ocular axis is defined as being the axis passing through the object focused on by the subject and the center of the exit pupil of the left eye.

The so-called "far-vision position" corresponds to the subject focusing on an object located at infinity in front of them, the sight line being horizontal. Since the image of the object is at infinity, the convergence angle of the two eyes is zero (the right and left ocular axes are parallel). Far vision is therefore associated with proximity parameters of zero (0 dioptres) and a gaze declination angle of zero. As a result of the proximity, the effective convergence angle is generally zero for far vision. The so-called "near-vision position" corresponds to the subject focusing on a nearby object in front of them (20 to 40 cm in front of them for example) the sight line being lowered. In the near-vision position the two eyes converge toward the image of the object. Near vision is therefore associated with non-zero proximity parameters (0.5 to 5 dioptres) and a non-zero gaze declination angle (comprised between 15 and 60 degrees). An intermediate vision position (IV), intermediate in terms of proximity (0.5 D) and gaze declination angle (declination angle of 15 degrees), for example corresponds to the comfortable distance for reading a computer screen.

The optimal correction of a corrective multifocal or progressive lens varies not only as a function of the proximity of a target but also conjointly as a function of the declination of the gaze. Studies that have examined the kinematics of the eyes of a subject as a function of the declination of the gaze have allowed the movement of the eyes, between a natural far-vision position (gaze axis horizontal) to a natural near-vision position (gaze axis lowered, for example in order to read a paper document) to be studied. The two eyes are observed not only to converge, which results in a change in the interpupillary distance, but also, nonlimitingly, each eye is observed to rotate about its ocular axis, the pressure of the lower eyelid on the cornea is observed to increase, and the lens is observed to decenter with the accommodation. It follows that the orientation of the physiological axis and value of the astigmatism of an eye vary when the eye passes from a natural far-vision position to a natural near-vision position. However, this variation in astigmatism between the near-vision and far-vision positions is generally not taken into account when parameterizing a corrective multifocal lens or a corrective progressive lens. More generally, it would be desirable to be able to measure ocular correction parameters (sphere, cylinder, axis, higher-order aberrations, keratometry, corneal topography, etc.) with precision as a function of the proximity of the target and as a function of the declination of the gaze, in order to be able to correct vision as a function of the natural position of the eye.

Various embodiments of the device of the invention will now be described in detail, which embodiments allow binocular or monocular ophthalmological measurements to be carried out in a plurality of binocular or monocular sight directions of the subject, in particular in order to allow a far-vision measurement and a vision measurement at a smaller distance (a near-vision and/or intermediate-vision distance inter alia) to be carried out.

Device

Figure 1:
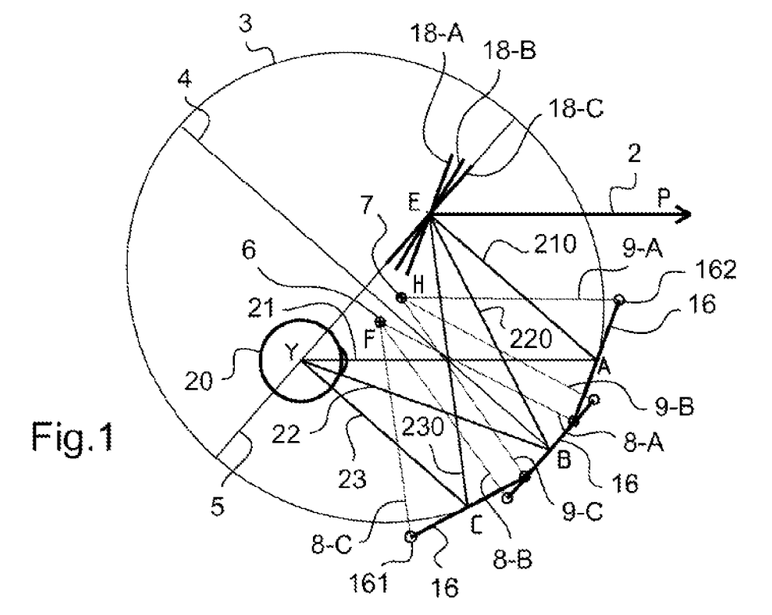
FIG. 1 schematically shows a device according to a first embodiment of the invention.

FIG. 1 shows a side view of a binocular or monocular optometric device along a plurality of sight directions according to a first embodiment of the invention. The optometric device comprises an external measuring system (not shown) securely fastened to the device, the external measuring system for example employing ocular reflection and/or refraction and comprising a variable proximity target for stimulating accommodation and/or convergence by the subject along a binocular or monocular sight direction. The measuring system emits a light beam along a measuring optical axis 2 intended to be directed toward the eye 20 of the subject to be measured. The measuring system collects the light beam originating from refraction and/or reflection from the eye in question along the same measuring optical axis 2. A target or stimulus test pattern emits a light beam intended to be directed toward the eye 20 of the subject to be measured, superposed on the sight axis of the eye in question.

FIG. 1 shows an ellipse 3 having a small axis 4 and a large axis 5, a first focal point Y and a second focal point E. Ideally, the optical center of rotation (OCR) of the eye 20 to be measured is merged with the first focal point Y of the ellipse 3. In practice, the device comprises adjusting means for bringing the first focal point Y into the vicinity of the OCR of the right eye 20. For example, the device comprises a headrest, comprising a chin rest and a forehead brace allowing the head to be kept in a set position, and means for adjusting the relative distance between the headrest and the first mirror 16. Preferably, the head rests on the chin rest, and the distance between the first focal point Y and the optical center of rotation of the eye 20 is adjusted via the field of view of the measuring system so that the pupil of the eye is always seen along all the sight directions considered for measurement. The OCR of the eye must be located so that the image of the pupil formed by the optical system consisting of the two mirrors 16 and 18 is not shifted by more than 10 mm from the measuring axis 2 for all the sight directions. Thus, the image of the pupil remains sharp enough that the measurement can be carried out along the desired sight directions, on account of the depth of field of the measuring system.

The second focal point of the ellipse 3 is placed at a point E on the measuring optical axis 2 of the ophthalmological measuring apparatus. The measuring device furthermore comprises an optical system placed between the eye 20 of the subject and the measuring optical axis 2. In the embodiment in FIG. 1, the optical system is a mirror-based optical system composed of a first mirror 16 and a second mirror 18. The planar first mirror 16 redirects the sight direction toward the first focal point E of the ellipse 3, and the planar second mirror 18 redresses the image of the sight axis formed by the first mirror in order to align it with the optical axis of the measuring apparatus for a plurality of sight directions of the subject. For this purpose, the planar mirror 16 is tangent to the ellipse 3. In this first embodiment, the planar first mirror 16 and the planar second mirror 18 are translationally and/or rotationally movable as a function of the sight direction of the subject. FIG. 1 shows, projected onto the sagittal plane, the ocular axis of the right eye 20 of a subject in three positions: in a far-vision position the horizontal right ocular axis is represented by a straight segment 21, in a near-vision position the right ocular axis, inclined by about 40 degrees, is represented by a straight segment 23, and in an intermediate-vision position the right ocular axis, inclined by about 20 degrees, is represented by a straight segment 22. Three optical pathways between the point Y and the point E, corresponding to the far-vision, intermediate-vision, and near-vision ocular axes, respectively, have been shown. An optical beam propagating along the segment 21 and incident on the first mirror 16 at a point A is reflected by the mirror 16 along the axis 210 in the direction of the point E. Analogously, an optical beam propagating along the segment 22, 23, respectively, and incident on the first mirror 16 at point B, C, respectively, is reflected by the mirror 16 along the axis 220, 230, respectively, in the direction of the point E. The planar second mirror 18 is arranged on the optical path of the measuring apparatus, the measuring optical axis 2 being incident on the planar second mirror 18 at the point E. Advantageously, the second mirror 18 is rotatably movable about the point E. FIG. 1 shows the second mirror 18 oriented along three orientations 18-A, 18-B and 18-C. The orientations 18-A, 18-B and 18-C are chosen in such a way that a beam propagating along the direction 210, 220 or 230, respectively, is reflected from the mirror 18 along the orientation 18-A, 18-B or 18-C, respectively, and propagates in the direction of the measuring apparatus along the measuring axis 2. Reciprocally, an illuminating beam originating from the measuring apparatus and propagating along the measuring axis 2 is incident on the second mirror 18 at the point E. Depending on the orientation 18-A, 18-B or 18-C, respectively, of the second mirror 18, the illuminating beam is reflected in a direction 210, 220 or 230, respectively. The optical system formed by the first mirror 16 and the second mirror 18 allows the measuring axis 2 passing through the point E and the sight axis passing through the point Y, and vice versa, to be aligned optically for a plurality of sight directions 21, 22, 23. Therefore, the illuminating beam originating from the point E and following the optical axis 210, 220 or 230, respectively, is reflected in the direction 21, 22 or 23, respectively, of the ocular axis. The optical system formed by the movable first mirror 16 and the orientable second mirror 18 allows the measuring optical axis 2 of a stationary apparatus and the sight axis of the subject to be optically aligned for a plurality of sight directions. In an FV first measuring position, the first mirror 16 is tangent to the ellipse 3 at a point A, and the second mirror has an orientation 18-A. In an IV second measuring position, the first mirror 16 is tangent to the ellipse 3 at a point B and the second mirror has an orientation 18-B. In an NV third measuring position, the first mirror 16 is tangent to the ellipse 3 at a point C and the second mirror has an orientation 18-C. In the position 18-A, the normal to the second mirror 18 is aligned with the bisector between the measuring optical axis 2 and the axis 210. In the position 18-B, the normal to the second mirror 18 is aligned with the bisector between the measuring optical axis 2 and the axis 220. In the position 18-C, the normal to the second mirror 18 is aligned with the bisector between the measuring optical axis 2 and the axis 230. Since the points A, B and C are tangents to the ellipse 3 the focal points of which are the point Y and the point E, the system allows an identical optical pathway YAE, YBE and YCE to be preserved for the sight directions 21, 22 and 23.

Alternatively, the first mirror 16 is a concave, spherical, elliptical or ellipsoidal mirror and the second mirror 18 is a mirror of non-zero power such that the optical system composed of the mirrors 16 and 18 is a focal to the 1st order of aberrations.

Those skilled in the art will be able to provide a cam, a guiding system, a system of hinged link connecting rods or any other simple mechanical system allowing the first mirror 16 to be moved along a trajectory approaching an elliptical trajectory.

In the embodiment shown in FIG. 1, the first mirror 16 is mounted on a system of link connecting rods 8, 9 so as to be able to move both translationally and rotationally. A first link connecting rod 8 comprises a first end connected to a link connecting rod fastening point 6 and a second end connected to the mirror 16 via a link connecting rod fastening point 161. A second link connecting rod 9 comprises a first end connected to a link connecting rod fastening point 7 and a second end connected to the mirror 16 via a link connecting rod fastening point 162. The system comprising the link connecting rods 8 and 9 hinges so that the movement of the first mirror 16 is tangent to the ellipse 3. The hinged system comprising the link connecting rods may be dimensioned in the following way. At least three positions of the first mirror 16 (corresponding to the points A, B and C, respectively) are placed on the ellipse 3 (for example, the two extreme positions A, C and a halfway position B). The first mirror 16 is dimensioned by its useful aperture, found by tracing rays of the measuring system for all the ocular axis positions, 21, 22 and 23, respectively. Two points for fastening the link connecting rods 161, 162 to the first mirror 16 are chosen. The link connecting rods 8, 9 each occupy at least three positions 8-A, 8-B, 8-C and 9-A, 9-B and 9-C, respectively. For each of the two fastening points of the links 161, 162, the center of the circle passing through the three successive positions is calculated. The two centers F and H, respectively, correspond to stationary points for fastening the link connecting rods 6 and 7, respectively. Next, the positions of the fastening points of the links 161, 162 on the first mirror 16 may be optimized in order to minimize alignment errors between the axis AE propagated toward the eye and the eye for the intermediate positions. Moreover, certain parameters may be optimized for (size of the ellipse 3, etc.) or imposed by cost, bulk or weight constraints.

Alternatively, a cam-based system for moving the mirror 16 may be used instead of a hinged system based on link connecting rods.

Whatever the moving system chosen (link connecting rods, cam or another system) for making the first mirror move tangent to the ellipse 3, the length of the optical pathway between the points E and Y remains constant whatever the optical pathway Y-A-E, Y-B-E or Y-C-E. In addition, the axis EP does not vary as a function of the direction of the sight axis. The optical system formed by the mirrors 16 and 18 allows the measuring optical axis 2 to be aligned with an image of the ocular axis along various gaze sight directions 21, 22, 23, respectively. The first embodiment makes it possible to carry out ophthalmological measurements as a function of sight direction over a wide angular range. The hinged system based on link connecting rods makes it possible to use a first mirror 16 of limited size, and therefore of relatively small cost.

The device in FIG. 1 makes it unnecessary to move an ophthalmological measuring apparatus to align it on the ocular axis of the subject. By definition, the optical path between the point Y and the point E is constant whatever the path followed, i.e. whatever the sight direction. The optical conjugating system has the advantage of not modifying the length of the optical pathway between the eye and the measuring apparatus, whatever the binocular or monocular sight direction. It is therefore not necessary to modify the sharpness of a target for the various measuring positions and for focus on the eye.

Figure 2:
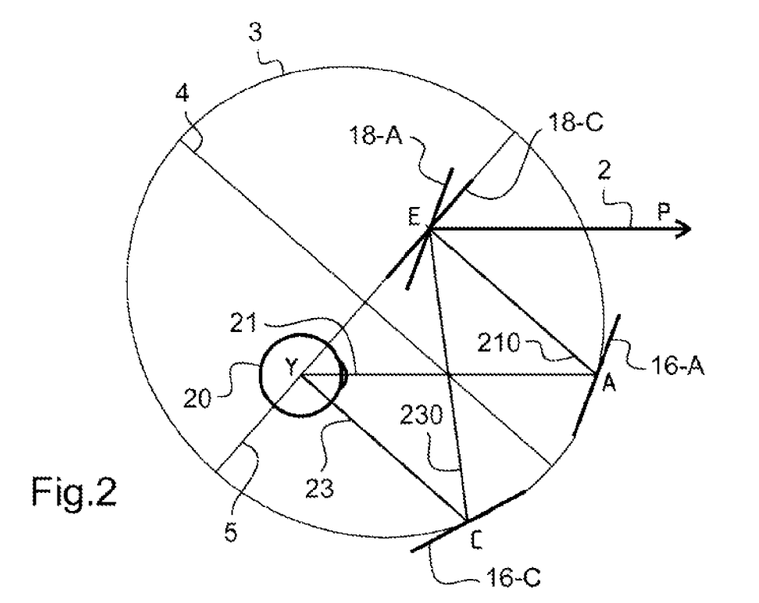
FIG. 2 schematically shows a device according to a first variant of the first embodiment of the invention.

FIG. 2 shows a side view of a binocular or monocular optometric device according to a variant of the first embodiment of the invention. FIG. 2 is a simplified variant of the first embodiment in FIG. 1. The same elements are designated by the same reference numbers as in FIG. 1. The measuring device also comprises a measuring apparatus (not shown) having a measuring axis 2 and a mirror-based optical system. In FIG. 2, the optical system comprises a set of two mirrors 16-A and 16-C and a planar second mirror 18, which mirrors are analogous to those of the device in FIG. 1. In this variant, the mirrors 16-A and 16-C are respectively fixed in two preset positions A and C. The second mirror 18 is an orientable planar mirror also having two preset positions 18-A and 18-C. The device in FIG. 2 allows measurements to be carried out along two binocular or monocular sight directions, for example corresponding to a far-vision measurement and a near-vision measurement. The device in FIG. 2 especially allows a FV/NV differentiated measurement to be carried out. In the two positions, the mirrors 16-A and 16-C are tangent to the ellipse, and the points E and Y are optically conjugated. The mirror 18 is rotationally movable about the point E, between the first position 18-A and the second position 18-C. These two positions are preset. The system for rotationally driving the second mirror may be simplified to a system switching between two stops. According to this second embodiment, the mirror 16-A is tangent to the ellipse 3 at the point A of intersection with the sight line 21, and the mirror 16-C is tangent to the ellipse 3 at the point C of intersection with the sight line 23. The image of the sight line 21 formed by the mirror 16-A passes through the point E. Likewise, the image of the sight line 23 formed by the mirror 16-C passes through the point E. Thus, the length of the optical pathway Y-A-E when the sight axis is oriented along the axis 21 is identical to the length of the optical pathway Y-C-E when the sight axis is oriented along the axis 23. Furthermore, when the mirror 18 is oriented in the position 18-A the image of the sight line 21 formed by the mirror 16-A and the mirror 18 in the position 18-A is superposed with the measuring axis 2. Likewise, when the mirror 18 is oriented in the position 18-C the image of the sight line 23 formed by the mirror 16-C and the mirror 18 in the position 18-C is superposed on the measuring axis 2.

Figure 3:
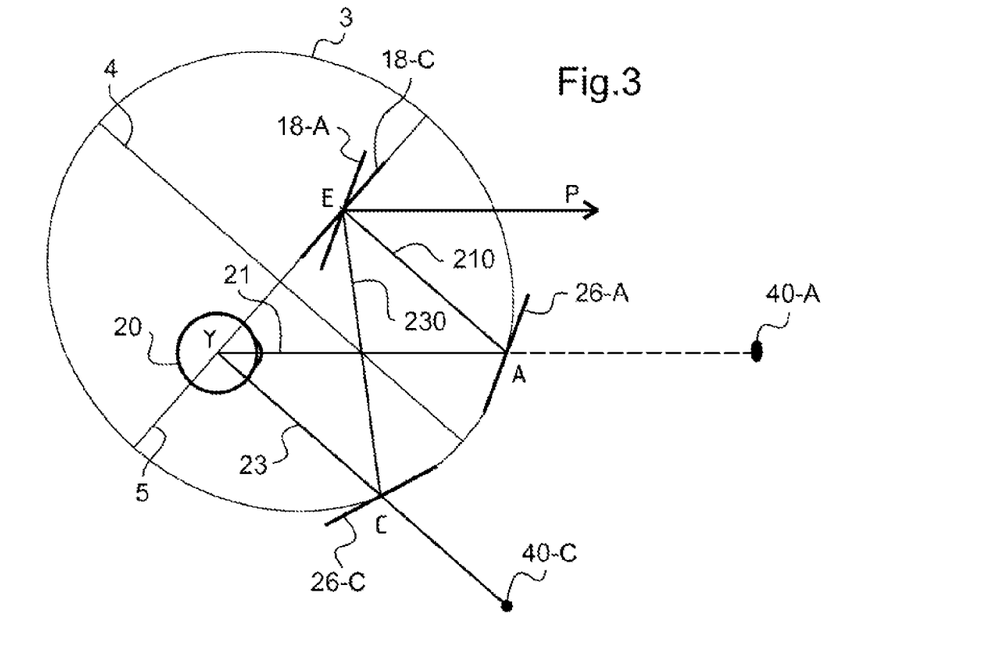
FIG. 3 schematically shows a device according to a second variant of the first embodiment of the invention.

FIG. 3 shows a second variant of the embodiment in FIG. 2. The device in FIG. 3 comprises two test patterns 40-A and 40-C of different proximities, which test patterns 40-A and 40-C are separate from the ophthalmological measuring apparatus. By way of nonlimiting and illustrative example, the test pattern 40-A has a proximity corresponding to a far-vision position, and the test pattern 40-C has a proximity corresponding to a near-vision position. In this second variant, the mirrors 16-A and 16-C are replaced by dichroic plates 26-A and 26-C, respectively, that are what are called hot mirrors. The hot mirrors 26-A and 26-C are able to transmit a visible beam (400-700 nm) and to reflect a beam in the near infrared (750-1100 nm). An ellipse 3 having for focal points a point Y and a point E is defined. The point Y is intended to be superposed on the OCR of the measured eye. The hot mirror 26-A is tangent to the ellipse 3 at the point A, and the hot mirror 26-C is tangent to the ellipse 3 at the point C. The mirror 18 cuts the measuring optical axis 2 at the point E and pivots about the point E between a position 18-A and a position 18-C.

In a first measuring position, the test pattern 40-A emits an optical stimulating beam in the visible so as to stimulate far-vision accommodation by the subject, whereas the test pattern 40-C is turned off. The mirror 18 is then in the position 18-A. The hot mirror 26-A transmits the visible optical stimulating beam so that the optical axis of the stimulating beam is superposed on the sight direction 21 that passes through the point A and the point Y. The measuring apparatus generates an illuminating beam in the near infrared, which beam is aligned with the measuring optical axis 2. The mirror 18 in the position 18-A reflects the illuminating beam in the direction 210 passing through the point E and the point A. The hot mirror 26-A reflects the near-infrared illuminating beam in the direction of the sight axis 21, corresponds to a far-vision sight direction. The measuring beam is formed by reflection and/or refraction of the illuminating beam from the eye 20 in the sight direction 21. The hot mirror 26-A reflects the measuring beam in the direction 210 toward the point E on the mirror 18. The mirror 18 in position 18-A reflects the measuring beam along the measuring axis 2. Thus, the device allows an ophthalmological measurement to be carried out, the eye being oriented along a first sight direction 21.

In another measuring position, the test pattern 40-C emits an optical stimulating beam in the visible so as to stimulate near-vision accommodation by the subject, whereas the test pattern 40-A is turned off. The mirror 18 is then in the position 18-C. The hot mirror 26-C transmits the visible optical stimulating beam so that the optical axis of the stimulating beam is superposed on another sight direction 23 that passes through the point C and the point Y. The measuring apparatus generates an illuminating beam in the near infrared, which beam is aligned with the measuring optical axis 2. The mirror 18 in position 18-C reflects the illuminating beam in the direction 230 passing through the point E and the point C. The hot mirror 26-C reflects the near-infrared illuminating beam in the direction of the sight axis 23, corresponds to a near-vision sight direction. The measuring beam is formed by reflection and/or refraction of the illuminating beam from the eye 20 in the sight direction 23. The hot mirror 26-C reflects the measuring beam in the direction 230 toward the point E on the mirror 18. The mirror 18 in position 18-C reflects the measuring beam along the measuring axis 2.

According to the second variant of the first embodiment, as illustrated by FIG. 3, the optical system formed by the hot mirrors 26-A, 26-C and the pivoting mirror 18 allow the measuring optical axis 2 to be aligned with a far-vision sight direction 21 and with a near-vision sight direction 23, along two optical pathways, E-A-Y and E-C-Y, respectively, having the same optical length.

Figure 4:
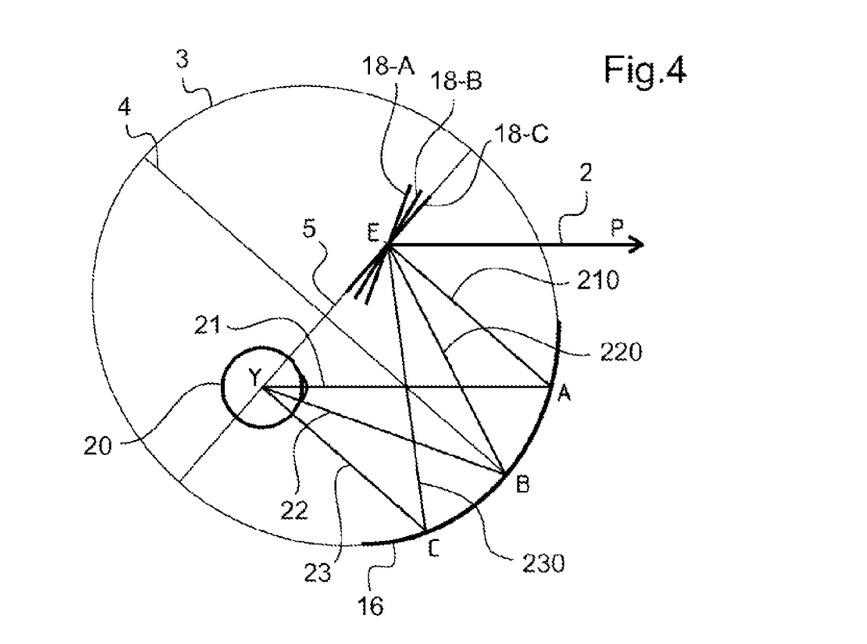
FIG. 4 schematically shows a device according to a second embodiment of the invention.

FIG. 4 shows a side view of an optometric device as a function of the sight direction according to a second embodiment of the invention. The device in FIG. 4 comprises an optical system formed by a first mirror 16 and a second mirror 18. Advantageously, the first mirror 16 is formed by a portion of the ellipse 3 and has for optical focal points the points E and Y. The directing second mirror 18 is a mirror of non-zero optical power or a deformable mirror able to correct the optical aberrations of the first mirror 16. The second mirror 18 is pivotably mounted about the point E. In contrast to the first embodiment, the ellipsoidal first mirror 16 remains stationary. By definition, the points E and Y are optically conjugated via the first mirror 16. Three measuring positions have been shown in FIG. 4, which positions correspond to three binocular or monocular sight directions. An optical beam propagating along the segment 21 and incident on the first mirror 16 at a point A is reflected by the mirror 16 along the axis 210 in the direction of the point E. Likewise, an optical beam propagating along the segment 22, 23, respectively, and incident on the first mirror 16 at a point B, C, respectively, is reflected by the mirror 16 along the axis 220, 230, respectively, in the direction of the point E. The second mirror 18 is orientable along at least three positions 18-A, 18-B and 18-C, respectively, so as to redress the image of the ocular axis via the first mirror 16 in order to align it with the measuring optical axis 2. In the position 18-A, the normal to the second mirror 18 is aligned with the bisector between the measuring optical axis 2 and the axis 210. In the position 18-B, the normal to the second mirror 18 is aligned with the bisector between the measuring optical axis 2 and the axis 220. In the position 18-C, the normal to the second mirror 18 is aligned with the bisector between the measuring optical axis 2 and the axis 230. Advantageously, the second mirror 18 is a deformable mirror for compensating the aberrations of the first mirror 16 as a function of the monocular or binocular sight direction, i.e. as a function of the orientation of the mirror 18. The correcting deformation applied to the second mirror 18 may be preset as a function of the orientation of the second mirror 18. The ellipsoidal first mirror 16 allows the optical center of rotation of the eye merged with the point Y to be optically conjugated with the point E on the measuring optical axis 2 with an optical pathway length that remains constant for various binocular or monocular sight directions. The second mirror 18 allows the image of the ocular axis to be redressed and aligned with the measuring optical axis 2. The optical conjugating system in FIG. 4 illustrates operation for three measuring positions. However, the ellipsoidal first mirror 16 makes it possible to take measurements over a continuous range of binocular or monocular gaze sight directions. Other measurements are possible in other binocular or monocular sight directions. It is enough to orient the second mirror 18 as a function of the binocular or monocular sight direction, so that the measuring optical axis 2 is aligned with the image of the ocular axis, for a particular binocular or monocular sight direction, via the optical conjugating system. The advantage of the device in FIG. 4 is that only one component, the second mirror 18, needs to be moved, the first mirror 16 remaining stationary. In this embodiment, a single rotational movement of the planar second mirror 18 is enough to align the measuring optical axis 2 with the image of the ocular axis for the various sight directions. However, the measuring range, as a function of the binocular or monocular sight direction, is related to the extent of the ellipsoidal mirror. The wider the desired angular measuring range, the higher the cost of the ellipsoidal mirror and the harder it is to correct for aberrations.

The device described with regard to FIGS. 1 to 4 enables binocular or monocular measurement along a plurality of sight directions.

The plane of FIGS. 1 to 4, containing the axis 5 of the ellipse 3, may lie parallel to the sagittal plane if the variation in the gaze direction corresponds to a declination of the gaze without a converging movement; alternatively, the plane of FIGS. 1 to 4, containing the axis 5 of the ellipse 3, may lie parallel to the Frankfurt plane if the variation in the direction of the gaze corresponds to a binocular convergence without variation in the declination of the gaze. In the case of a combination of a lowering movement and convergence of the gaze, the plane of FIGS. 1 to 4 may be a plane inclined at a set inclination relative to the sagittal plane. According to one advantageous embodiment, the device comprises rotating means able to make the plane containing the axis 5 of the ellipse 3 turn about the axis 5. According to yet another embodiment, the plane of the ellipse 3 may be inclined about the axis YA, the declination and convergence being related in a preset way.

Figure 5:
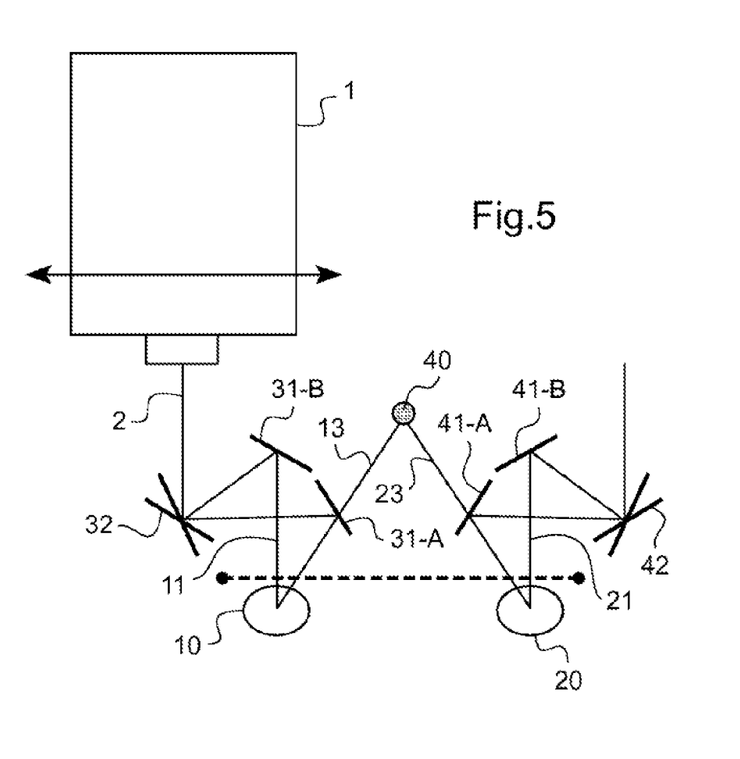
FIG. 5 schematically shows a device according to a third embodiment of the invention.

FIG. 5 shows an ophthalmological measuring system according to a third embodiment of the invention. The device comprises a monocular measuring apparatus 1 able to carry out a monocular measurement along a measuring optical axis 2. Preferably, the measuring apparatus 1 comprises an internal target able to generate an optical stimulating beam for far-vision stimulation. The monocular measuring apparatus 1 is translationally movable (horizontal arrow) in order to allow it to be placed opposite the eye to be measured. The device in FIG. 5 comprises a binocular target 40 able to stimulate accommodation and convergence by both eyes simultaneously. Advantageously, the target 40 has a proximity corresponding to a near-vision position. The device also comprises an optical aligning system for each eye, so as to allow measurements to be carried out along a plurality of gaze sight directions without modifying the optical pathway length. An optical system comprising two hot mirrors 31-A, 41-A is located as close as possible to the eyes in order to allow NV accommodation and convergence to be stimulated. The point focused on 40 is located at a proximity between 0.5 and 10 dioptres in the sagittal plane in order to solicit ocular convergence. Advantageously, the hot mirrors 31-A, 41-A and the target 40 are arranged so as to combine a declination and a convergence of the binocular NV gaze. The hot mirrors 31-A and 41-A allow the point focused on 40 to be observed in the visible while reflecting the infrared measuring beam toward a pivoting mirror 32 or 42, respectively, and in the direction of the measuring axis 2 of the monocular measuring apparatus 1. When the NV target 40 is turned on, the device thus allows a monocular measurement to be carried out in a NV sight direction, 13 for the left eye 10 and 23 for the right eye 20, respectively. The device furthermore comprises hot mirrors 31-B, 41-B arranged so as to allow a FV measurement to be carried out in a FV sight direction, 11 for the left eye 10 and 21 for the right eye 20, respectively. The orientable mirrors 32, 42 make it possible to pass from a FV measuring position to another NV measuring position, and vice versa. In the FV position the eyes sees the stimulus of the measuring apparatus 1, which is therefore monocular. In contrast, in the NV position the stimulus 40 is seen by both eyes, making it possible to lower the gaze and obtain convergence on and accommodation to a single point. Thus the monocular measuring apparatus allows a FV measurement and a NV measurement to be carried out. The mirror 31-A, the mirror 31-B, respectively, is placed so as to be tangent at a point A, at a point B, respectively, to an ellipse having for focal points a point Y aligned on the OCR of the left eye 10 and a point E located at the intersection of the measuring axis 2 with the mirror 32. Likewise, the mirror 41-A, the mirror 41-B, respectively, is placed so as to be tangent at a point A', at a point B', respectively, to an ellipse having for focal points a point Y' aligned on the OCR of the right eye 20 and a point E' located at the intersection of the measuring axis 2 with the mirror 42. In this way, the optical pathway between the OCR of the measured eye and the ophthalmological measuring apparatus 1 is identical in the NV and FV sight directions.

Figure 6A:
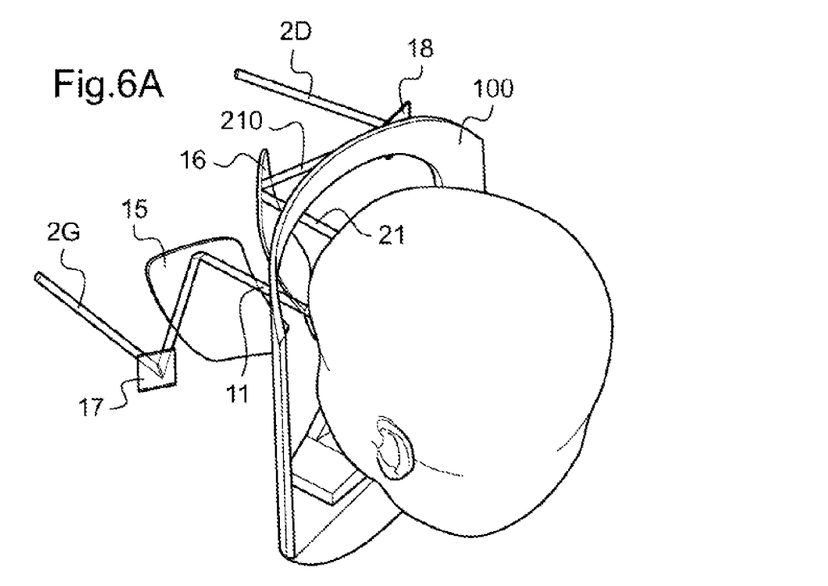
FIGS. 6A to 6F schematically show various views of a binocular device according to one preferred embodiment of the invention.
Figure 6B:
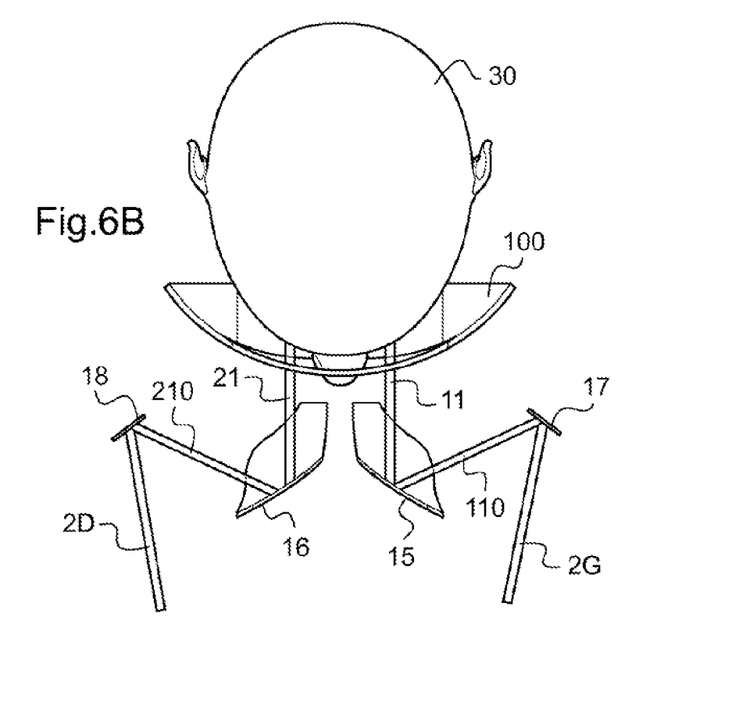
Figure 6C:
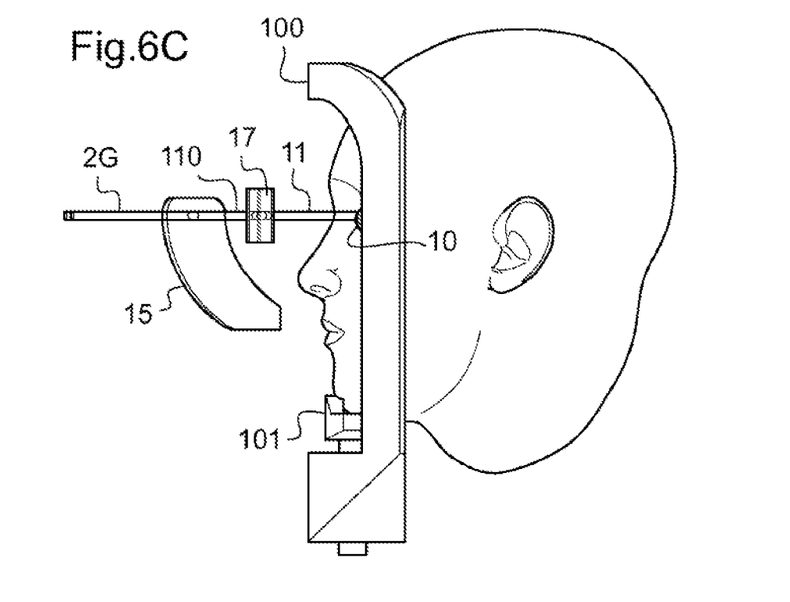
Figure 6D:
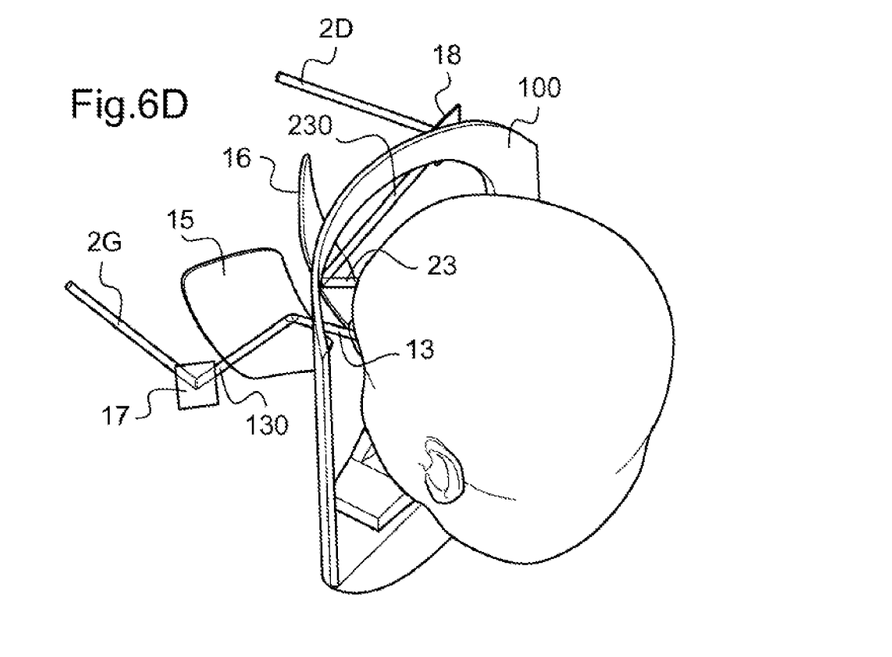
Figure 6E:
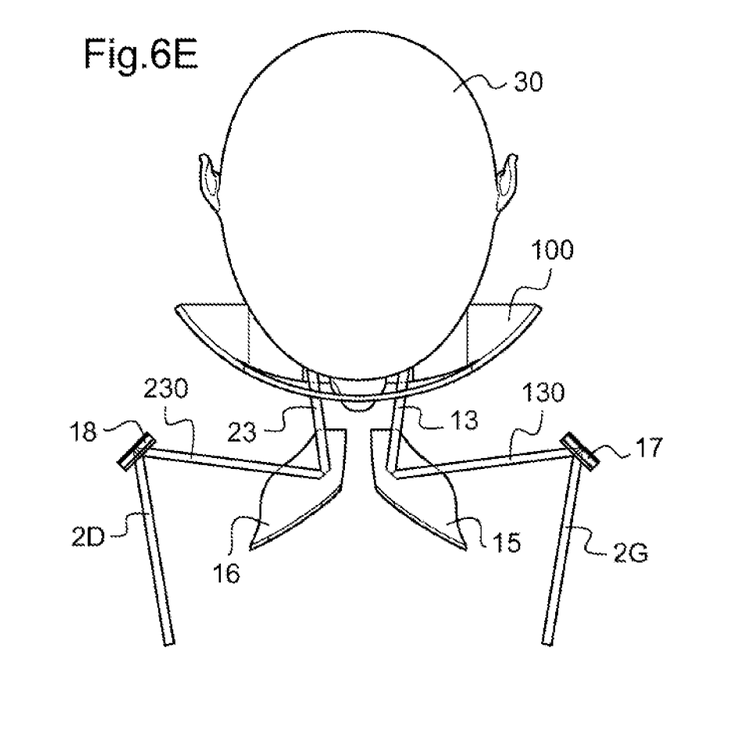
Figure 6F:
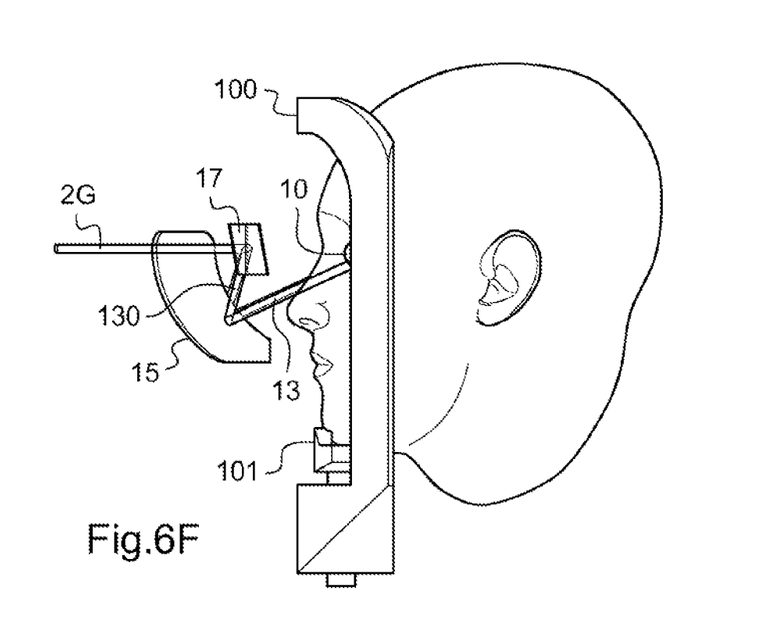

FIGS. 6A-6F schematically illustrate various views of a binocular device according to one preferred embodiment of the invention. It is a question of a variant of the device in FIG. 5, in which a translationally movable monocular measuring apparatus has been replaced by two monocular measuring apparatuses having a right measuring axis 2D and a left measuring axis 2G, respectively, which axes are dedicated to the right eye and to the left eye, respectively, in order to avoid the translational movement. FIGS. 6A, 6B and 6C illustrate the FV operation of the device, the sight line being horizontal. FIGS. 6D, 6E and 6F illustrate the NV operation of the device, the sight line being declined relative to the horizontal and the gaze being convergent. FIGS. 6A and 6D are perspective views of the measuring device, FIGS. 6B and 6E are top views and FIGS. 6B and 6E front views of the device. The same reference signs correspond to the same elements described with regard to the other embodiments. Only the optical aligning system has been shown in FIGS. 6A-6F, the other elements not being shown. The device comprises a binocular target able to stimulate accommodation and convergence by both eyes simultaneously. In FIGS. 6A and 6D, the measuring axis 2G of the left eye of the subject is shown in the foreground and the measuring axis 2D of the right eye of the subject is shown in the background. The device comprises a headrest 100 comprising a chin rest 101 and a zone against which the forehead may bear in order to keep the head 30 of the subject in a fixed position. Advantageously, the head of the subject is held in a position such that their Frankfurt plane is horizontal. For certain particular measurements, the headrest may be inclined so as to allow measurements to be carried out for other postures of the head of the subject. The device comprises a first optical system comprising a stationary ellipsoidal first mirror 16, a pivoting or rotationally movable second mirror 18, and an ophthalmological measuring apparatus dedicated to the right eye 20 and located along the measuring axis 2D. The device also comprises a second optical aligning system comprising a stationary ellipsoidal first mirror 15 (i.e. not a mirror that is movable along an elliptical trajectory), a pivoting or rotationally movable second mirror 17 of non-zero power, and an ophthalmological measuring apparatus dedicated to the left eye 10 and located along the measuring axis 2G. The device in FIGS. 6A-6F also comprises adjusting means that act on the part 101 of the chin rest 100 and/or on the optical aligning system in order to bring a focal point of the ellipsoidal mirror 15 into the vicinity of the optical center of rotation of the left eye 10. Likewise, adjusting means are provided for bringing a focal point of the ellipsoidal mirror 16 into the vicinity of the OCR of the right eye 20. The heights of the right and left optical aligning systems may be adjusted independently in order to align the measuring axes depending on the height of the eyes of the subject. Advantageously, the right and left optical aligning systems are coupled, in particular the orientation of the mirrors 17 and 18.

In FIGS. 6A-6C, the subject observes a test pattern in a vision posture corresponding to far vision: the right ocular axis 21 and the left ocular axis 11 are horizontal and substantially parallel to each other (to within errors in the vision of the subject). The ellipsoidal mirrors 15, 16, respectively, direct the left ocular axis 11 along a direction 110 and the right ocular axis 21 along a direction 210, respectively, toward the second mirror 17, 18, respectively. In this far-vision posture, the mirror 17 is oriented so as to align the image of the left ocular axis with the left measuring axis 2G, and respectively the mirror 18 is oriented so as to align the image of the right ocular axis with the right measuring axis 2D.

In FIGS. 6D-6F, the subject observes a test pattern in a vision posture corresponding to near vision: the right ocular axis 23 and the left ocular axis 13 are lowered and converge. The ellipsoidal mirrors 15, 16, respectively, direct the left ocular axis 13 along a direction 130 and the right ocular axis 23 along a direction 230, respectively, toward the second mirror 17, 18, respectively. The ellipsoidal mirrors 15, 16 remain stationary for the various measuring postures. In this near-vision posture, the mirror 17 is oriented so as to align the image of the left ocular axis 230 with the left measuring axis 2G, and respectively the mirror 18 is oriented so as to align the image of the right ocular axis 130 with the right measuring axis 2D.

The device in FIGS. 6A-6F allows a monocular measurement to be carried out for each eye along a plurality of binocular sight directions. The optical aligning system comprising the ellipsoidal mirrors 15 and 16, and the mirrors 17, 18 allows an ophthalmological measurement to be carried out along a plurality of gaze sight directions while ensuring the length of the optical pathway along the various gaze sight directions is kept constant. The left and right monocular measuring apparatuses remain stationary. Advantageously, only the second mirrors 17 and 18 are rotationally movable about a pivot point and compensate to the 1st order the aberrations generated by the ellipsoidal mirrors 15 and 16.

The value of the half-interpupillary distance parameter (½ IPD) may be adapted symmetrically or asymmetrically (adjusted by half-IPD) and on the basis of an exterior measurement (Visioffice or pupilometer) or on the basis of a FV recalibration of the apparatus during the alignment.

The invention is particularly suitable for anyone who takes refraction-based ophthalmological measurements and who wants to provide or carry out measurements that take into account physiological inclination of the eyes of the subject.

The device of the invention may be used by an optometrist or an ophthalmologist, or even by an optician in order to determine parameters for personalizing a spectacle glass.

The device and method and the invention may serve to define the means required to prescribe a progressive or multifocal corrective lens.

The invention allows a binocular or monocular ophthalmological measuring apparatus having an optical measuring axis for each eye to be adapted to allow measurements to be carried out along a plurality of binocular or monocular sight directions. Advantageously, the device of the invention allows far-vision/near-vision differentiated ophthalmological measurements that take the sight direction of the gaze into account to be carried out.

The invention claimed is:

1. A device for determining at least one vision parameter of a subject along a plurality of monocular or binocular sight directions of the subject, said device comprising:
   a binocular or monocular ophthalmological measuring apparatus comprising ophthalmological means for measuring the vision parameter to be determined, which means are able to emit an illuminating optical beam, and to receive a measuring optical beam along at least one measuring optical axis aligned with a preset sight direction of the eye in question;
   visual stimulating means able to generate a stimulating optical beam along a stimulating optical axis aligned with said preset sight direction of the eye in question; and
   head-supporting means able to receive the head of a subject and to keep it in a set posture,
characterized in that:
there being defined an ellipse having a first focal point on said measuring optical axis and a second focal point, said device comprises:
   at least one optical aligning system placed between the ophthalmological measuring means and the eye in question, said optical aligning system being able to reflect said illuminating and measuring optical beams between the focal points of the ellipse; and
   adjusting means able to modify the relative position of said optical aligning system relative to the head-supporting means so as to bring the second focal point into the vicinity of the center of rotation of the eye in question of the subject, said optical aligning system comprising first reflective optical means and second reflective optical means, said first reflective optical means being tangent to said ellipse at a first point in a first sight direction and at at least one other point in at least one other sight direction of the eye in question, and said second reflective optical means being mounted so as to be rotatably movable about the first focal point between a first position in which the optical aligning system aligns said first sight direction with the measuring optical axis and at least one other position in which the optical aligning system aligns said at least one other sight direction of the eye in question with the measuring optical axis.

2. The device for determining at least one vision parameter as claimed in claim 1, in which the first reflective optical means comprise a spherical mirror, a planar mirror, a plurality of planar mirrors, a dichroic plate or a plurality of dichroic plates.

3. The device for determining at least one vision parameter as claimed in claim 2, in which said first reflective optical means comprise a first mirror, and in which said optical aligning system comprises means for moving the first mirror, which means are able to move the first mirror along a preset trajectory as a function of the binocular or monocular sight direction of the subject.

4. The device for determining at least one vision parameter as claimed in claim 3, in which said means for moving the first mirror comprise a hinged system of link connecting rods, a cam and/or a mechanical guiding system.

5. The device for determining at least one vision parameter as claimed in claim 4, in which said second reflective optical means comprise a planar mirror.

6. The device for determining at least one vision parameter as claimed in claim 3, in which said preset trajectory is an elliptical trajectory, and in which said first mirror is oriented so as to be tangent to said elliptical trajectory.

7. The device for determining at least one vision parameter as claimed in claim 2, in which said first reflective optical means comprise a first mirror having a first preset position tangent to said ellipse at a first point, and a second mirror having a second preset position tangent to said ellipse at another point.

8. The device for determining at least one vision parameter as claimed in claim 7, in which said second reflective optical means comprise a planar mirror.

9. The device for determining at least one vision parameter as claimed in claim 1, in which said first reflective optical means comprise an ellipsoidal mirror, and said second reflective optical means comprise a second mirror having a non-zero optical power, so that the optical aligning system formed by the first and second mirrors is afocal to the first order.

10. The device for determining at least one vision parameter as claimed in claim 9, in which said second reflective optical means comprise a planar mirror.

11. The device for determining at least one vision parameter as claimed in claim 1, in which said second reflective optical means comprise a planar mirror.

12. The device for determining at least one vision parameter as claimed in claim 11, in which said aligning system comprises a means for orienting the second reflective optical means, able to make the second reflective optical means pivot about the first focal point of the ellipse as a function of the binocular or monocular sight direction.

13. The device for determining at least one vision parameter as claimed in claim 1, in which said aligning system comprises a means for orienting the second reflective optical means, able to make the second reflective optical means pivot about the first focal point of the ellipse as a function of the binocular or monocular sight direction.

14. The device for determining at least one vision parameter as claimed in claim 1, comprising means for inclining said optical aligning system, said inclining means being able to orient the plane of the ellipse about an axis passing through its focal points.

15. The device for determining at least one vision parameter as claimed in claim 1, in which said optical aligning system comprises at least one first preset position associated with a first sight direction, and at least one other preset position associated with at least one other sight direction.

16. The device for determining at least one vision parameter as claimed in claim 15, in which said first sight direction corresponds to a horizontal direction straight in front of the subject, and in which said at least one other sight direction corresponds to a near-vision sight direction that is inclined relative to the horizontal.

17. The device for determining at least one vision parameter as claimed in claim 1, in which the ophthalmological measuring means are able to measure and record at least one vision parameter such as sphere, cylinder, axis, higher-order aberration, a keratometry and/or corneal topography type parameter, and/or pupil diameter in a first sight direction and in at least one other sight direction, and/or a difference between a vision parameter measured in said first sight direction and measured in said at least one other sight direction.

18. The device for determining at least one vision parameter as claimed in claim 1, in which said ophthalmological measuring apparatus is a binocular apparatus having a first measuring axis associated with the right eye of the subject and a second measuring axis associated with the left eye of the subject, and wherein said at least one optical aligning system consists of a first optical aligning system and a second optical aligning system, the first optical aligning system being intended to be placed between said binocular ophthalmological measuring apparatus and the right eye of the subject; and the second optical aligning system, being intended to be placed between said binocular ophthalmological measuring apparatus and the left eye of said subject.

* * * * *